US008143291B2

United States Patent
Beard et al.

(10) Patent No.: US 8,143,291 B2
(45) Date of Patent: *Mar. 27, 2012

(54) INDOLE COMPOUNDS BEARING ARYL OR HETEROARYL GROUPS HAVING SPHINGOSINE-1-PHOSPHATE (S1P) RECEPTOR BIOLOGICAL ACTIVITY

(75) Inventors: Richard L. Beard, Newport Beach, CA (US); Haiqing Yuan, Irvine, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 146 days.

This patent is subject to a terminal disclaimer.

(21) Appl. No.: 12/983,385

(22) Filed: Jan. 3, 2011

(65) Prior Publication Data

US 2011/0275677 A1 Nov. 10, 2011

Related U.S. Application Data

(62) Division of application No. 12/679,530, filed on May 6, 2010, now Pat. No. 7,888,336.

(60) Provisional application No. 61/051,779, filed on May 9, 2008.

(51) Int. Cl.
| | |
|---|---|
| A61K 31/4439 | (2006.01) |
| A61K 31/422 | (2006.01) |
| A61K 31/404 | (2006.01) |
| A61K 31/429 | (2006.01) |
| A61P 27/06 | (2006.01) |
| A61P 27/00 | (2006.01) |
| A61P 9/00 | (2006.01) |
| A61P 17/02 | (2006.01) |
| C07D 417/14 | (2006.01) |
| C07D 413/14 | (2006.01) |
| C07D 413/06 | (2006.01) |
| C07D 401/06 | (2006.01) |
| C07D 513/04 | (2006.01) |
| C07D 409/06 | (2006.01) |
| C07D 209/08 | (2006.01) |

(52) U.S. Cl. ........ 514/339; 514/366; 514/374; 514/414; 514/419; 546/269.7; 546/271.4; 546/277.4; 548/151; 548/235; 548/468; 548/503

(58) Field of Classification Search .................. None
See application file for complete search history.

(56) References Cited

U.S. PATENT DOCUMENTS

| | | | |
|---|---|---|---|
| 4,952,683 A | 8/1990 | Tschannen et al. | |
| 5,102,901 A | 4/1992 | van Wijngaarden et al. | |
| 5,110,987 A | 5/1992 | Liotta et al. | |
| 5,294,722 A | 3/1994 | Kim | |
| 5,403,851 A | 4/1995 | D'Orlando et al. | |
| 5,580,878 A | 12/1996 | D'Orlando et al. | |
| 6,235,912 B1 | 5/2001 | Takesako et al. | |
| 6,239,297 B1 | 5/2001 | Takesako et al. | |
| 6,566,533 B1 * | 5/2003 | Barth et al. | 548/441 |
| 6,630,496 B1 * | 10/2003 | Seehra et al. | 514/369 |
| 2003/0125371 A1 | 7/2003 | Elokdah et al. | |

FOREIGN PATENT DOCUMENTS

| | | |
|---|---|---|
| WO | WO 03/062252 A1 | 7/2003 |
| WO | WO 2003/062392 A2 | 7/2003 |
| WO | WO/2004/071442 | 8/2004 |
| WO | WO 2004/096752 A1 | 11/2004 |
| WO | WO 2004/103274 | 12/2004 |
| WO | WO 2004/103306 A2 | 12/2004 |
| WO | WO 2007/095561 | 8/2007 |
| WO | WO 2007/112322 | 10/2007 |

OTHER PUBLICATIONS

Clemens, J. J. et al. Bioorg. Med. Chem. Lett. 2003, 13, 3401.
Hale, J. J. et al. Bioorg. Med. Chem. Lett. 2004, 14, 3351.
Hale, J. J. et al. Bioorg. Med. Chem. Lett. 2004,14,3495.
Clemens, J. J. et al. Bioorg. Med. Chem. Lett. 2004,14,4903.
Hale, J. J. et al. Bioorg. Med. Chem. Lett. 2004, 14, 3501.
Hale, J. J. et al. J. Med. Chem. 2004, 47, 6662.
Domschke G et al: "N-Substituierte I-Benzyl -2-.Methyl -3-Aminomethyl-5-Methoxyindole Und Verwandte Verbindungen" Chemische Berichte, Verlag Chemie Gmbh. Weinheim, DE, vol. 93, Jan. 1, 1960, pp. 2097-2106.
Arai et al., caplus an 2004:516923.

\* cited by examiner

*Primary Examiner* — Sun Jae Loewe
(74) *Attorney, Agent, or Firm* — Doina G. Ene; John E. Wurst; Kevin J. Forrestal

(57) ABSTRACT

The invention provides well-defined aryl and/or heteroaryl substituted indoles that are useful as sphingosine-1-phosphate agonists or antagonists. As such, the compounds described herein are useful in treating a wide variety of disorders associated with modulation of sphingosine-1-phosphate receptors.

7 Claims, No Drawings

INDOLE COMPOUNDS BEARING ARYL OR HETEROARYL GROUPS HAVING SPHINGOSINE-1-PHOSPHATE (S1P) RECEPTOR BIOLOGICAL ACTIVITY

CROSS-REFERENCE

This application is a Divisional of U.S. patent application Ser. No. 12/679,530, filed May 6, 2010, which claims the benefit of national stage application under 35 U.S.C. §371 of PCT patent application PCT/US09/42725, filed on May 4, 2009 which claims the benefit of U.S. provisional patent application Ser. No. 61/051,779, filed on May 9, 2008, each of which is hereby incorporated by reference in its entirety.

FIELD OF THE INVENTION

The present invention relates generally to aryl and heteroaryl substituted indoles and to their use as agonists or antagonists, for example as agonists or antagonists of sphingosine-1-phosphate receptors. The invention relates specifically to the use of these compounds and pharmaceutical compositions to treat disorders associated with sphingosine-1-phosphate receptor modulation.

BACKGROUND OF THE INVENTION

Sphingosine is a compound having the chemical structure shown in the general formula described below, in which $Y^1$ is hydrogen. It is known that various sphingolipids, having sphingosine as a constituent, are widely distributed in the living body including on the surface of cell membranes of cells in the nervous system.

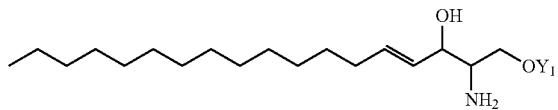

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by sphingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 µM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or sphingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

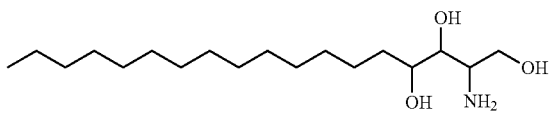

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

Derivatives of sphingosine have been prepared in various patents. For example, see U.S. Pat. Nos. 4,952,683; 5,110,987; 6,235,912 B1 and 6,239,297 B1.

Also, compounds which are similar to certain sphingosine derivatives, but which are not reported as being ligands for the sphingosine receptors are reported in various patents and published patent applications. See for example, U.S. Pat. Nos. 5,294,722; 5,102,901; 5,403,851 and 5,580,878. U.S. Patent Application Publication No. U.S. 2003/0125371 A2. While certain of the compounds reported in the above patents are indoles, it does not appear that indole compounds have been reported as being ligands for sphingosine receptor or having activity as sphingosine agonists or antagonists.

SUMMARY OF THE INVENTION

The invention provides well-defined aryl and/or heteroaryl substituted indoles that are useful as sphingosine-1-phosphate agonists or antagonists. As such, the compounds described herein are useful in treating a wide variety of disorders associated with modulation of sphingosine-1-phosphate receptors.

In one embodiment of the invention, there are provided compounds having the structure

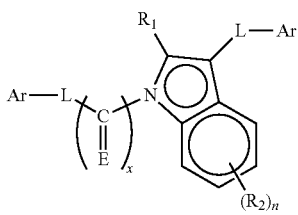

wherein:
each Ar is independently substituted or unsubstituted aryl or heteroaryl;
each L is independently alkylene, alkenylene, oxyalkylene, oxyalkenylene, aminoalkylene, or aminoalkenylene;
$R_1$ is lower alkyl, alkylacyl or hydroxyalkyl;
each $R_2$ is independently H, lower alkyl, halide, trifluoromethyl, lower alkenyl, lower alkynyl, cycloalkyl, —CN,
—$CH_2CN$, —$CH_2SR_3$, —$CH_2N(R_3)_2$, —$CH_2OR_3$, —CH=$NOR_3$, —$OR_3$, —$SR_3$, —$N(R_3)_2$, —$C(O)R_4$, heterocycle, substituted heterocycle, aryl, substituted aryl, heteroaryl, substituted heteroaryl; or
$R_2$ is

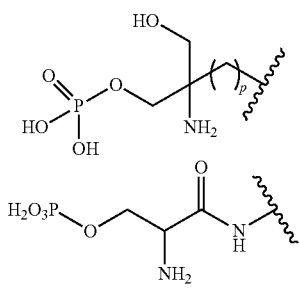

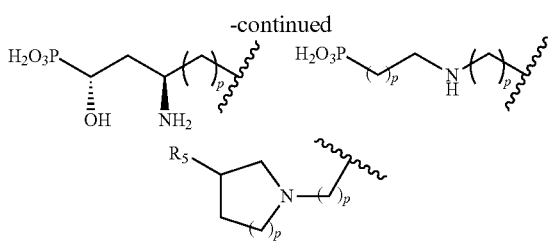

wherein $R_5$ is —$CO_2H$ or $PO_3H_2$ and p is 0-2; or
when n is 2, each $R_2$ taken together with carbon atoms to which each $R_2$ is attached forms an aryl, substituted aryl, heteroaryl, substituted heteroaryl, cycloalkyl or substituted cycloalkyl;
each $R_3$ is independently H, lower alkyl, cycloalkyl, allyl, phenyl, substituted phenyl, heteroaryl, or substituted heteroaryl;
each $R_4$ is independently H, lower alkyl, cycloalkyl, alkoxy, alkyamino, dialkylamino, phenyl, substituted phenyl, heteroaryl, substituted heteroaryl, or trifluoromethyl;
E is O or S;
x is 0 or 1; and
n is 0-5;
or pharmaceutically acceptable salts thereof.

In another embodiment, there are provided pharmaceutical compositions including at least one aryl and/or heteroaryl substituted indole of the invention in a pharmaceutically acceptable carrier therefor.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one aryl and/or heteroaryl substituted indole of the invention.

In still another embodiment of the invention, there are provided methods for treating disorders associated with modulation of sphingosine-1-phosphate receptors. Such methods can be performed, for example, by administering to a subject in need thereof a therapeutically effective amount of at least one aryl and/or heteroaryl substituted indole of the invention, or any combination thereof, or pharmaceutically acceptable salts, hydrates, solvates, crystal forms and individual isomers, enantiomers, and diastereomers thereof.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

As used herein, "alkyl" refers to straight, branched chain or cyclic hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents typically selected from alkyl, alkenyl, alkynyl, hydroxy, alkoxy, heterocyclic, aryl, heteroaryl, aryloxy, halogen, haloalkyl, cyano, nitro, amino, lower alkylamino, lower dialkylamino, amido, azido, acyl (—C(O)$R_6$), alkoxymethyl, mercapto (—S—$R_6$), sulfoxy (—S(O)—$R_6$), sulfonyl (—S(O)$_2$—$R_6$), sulfonamide (—S(O)$_2$N($R_6$)$_2$), carbonate (—OC(O)—O—$R_6$), oxyacyl (—OC(O)—$R_6$), carboxyl (—C(O)OH), ester (—C(O)O$R_6$), carbamate (—OC(O)—N($R_6$)$_2$), wherein $R_6$ is H or lower alkyl, lower alkenyl, lower alkynyl, aryl, heteroaryl, heterocycle, and the like. As used herein, "lower alkyl" refers to alkyl moieties having from 1 to about 6 carbon atoms.

As used herein, "alkenyl" refers to straight, branched chain or cyclic hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 1 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As employed herein, "alkylene" refers to saturated, divalent straight or branched chain hydrocarbyl groups typically having in the range of about 1 up to about 100 carbon atoms.

As employed herein, "oxyalkylene" refers to saturated, divalent straight or branched chain hydrocarbyl groups having at least one oxygen atom and typically having in the range of about 1 up to about 100 carbon atoms.

As employed herein, "alkenylene" refers to divalent straight or branched chain hydrocarbyl groups having at least one carbon-carbon double bond, and typically having in the range of about 2 up to 100 carbon atoms.

As employed herein, "oxyalkenylene" refers to divalent straight or branched chain hydrocarbyl groups having at least one oxygen atom and at least one carbon-carbon double bond, and typically having in the range of about 2 up to 100 carbon atoms.

As employed herein, "aminoalkylene" refers to saturated, divalent straight or branched chain hydrocarbyl groups having at least one nitrogen atom and typically having in the range of about 1 up to about 100 carbon atoms.

As employed herein, "aminoalkenylene" refers to divalent straight or branched chain hydrocarbyl groups having at least one nitrogen atom and at least one carbon-carbon double bond, and typically having in the range of about 2 up to 100 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heteroaryl" refers to heteroaryl groups further bearing one or more substituents as set forth above.

As used herein, "heterocyclic" or "heterocycle" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" or "substituted heterocycle" refers to heterocyclic groups or heterocycles further bearing one or more substituents as set forth above.

As used herein, "halogen" or "halide" refers to fluoride, chloride, bromide or iodide. The terms "fluoro", "chloro", "bromo", and "iodo" may also be used when referring to halogenated substituents, for example, "trifluoromethyl."

As used herein, "hydroxyalkyl" refers to alkyl-OH, such as hydroxymethyl, hydroxyethyl, and the like.

As used herein, "alkylacyl" refers to an alkyl ketone such as ethanone, propanone, and the like.

As used herein, "pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The invention provides compounds having the structure:

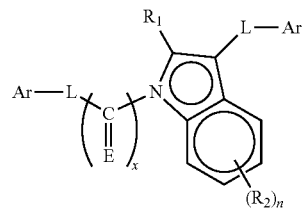

wherein:
    each Ar is independently substituted or unsubstituted aryl or heteroaryl;
    each L is independently alkylene, alkenylene, oxyalkylene, oxyalkenylene, aminoalkylene, or aminoalkenylene;
    $R_1$ is lower alkyl, alkylacyl or hydroxyalkyl;
    each $R_2$ is independently H, lower alkyl, halide, trifluoromethyl, lower alkenyl, lower alkynyl, cycloalkyl, —CN, —CH$_2$CN, —CH$_2$SR$_3$, —CH$_2$N(R$_3$)$_2$, —CH$_2$OR$_3$, —CH=NOR$_3$, —OR$_3$, —SR$_3$, —N(R$_3$)$_2$, —C(O)R$_4$, heterocycle, substituted heterocycle, aryl, substituted aryl, heteroaryl, substituted heteroaryl; or R$_2$ is

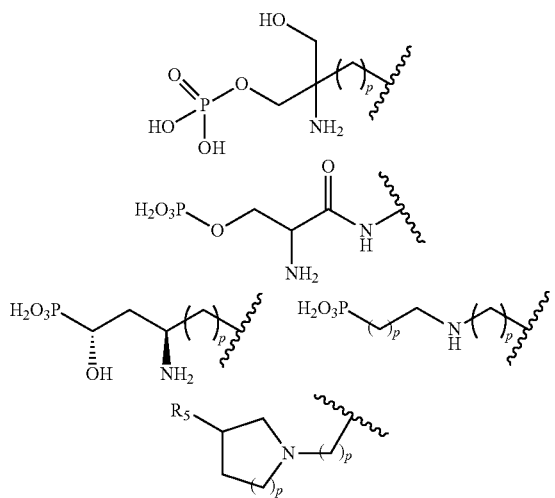

wherein R$_5$ is —CO$_2$H or PO$_3$H$_2$ and p is 0-2; or
when n is 2, each R$_2$ taken together with carbon atoms to which each R$_2$ is attached forms an aryl, substituted aryl, heteroaryl, substituted heteroaryl, cycloalkyl or substituted cycloalkyl;
each R$_3$ is independently H, lower alkyl, cycloalkyl, allyl, phenyl, substituted phenyl, heteroaryl, or substituted heteroaryl;
each R$_4$ is independently H, lower alkyl, cycloalkyl, alkoxy, alkylamino, dialkylamino, phenyl, substituted phenyl, heteroaryl, substituted heteroaryl, or trifluoromethyl;
E is O or S;
x is 0 or 1; and
n is 0-5;
or pharmaceutically acceptable salts thereof.

In some embodiments of the invention, there are provided aryl and/or heteroaryl substituted indoles according to the structure defined above wherein x is 1 and E is O.

In other embodiments, there are provided invention compounds wherein each Ar is independently selected from phenyl, pyridine, pyrazine, pyridazine, pyrimidine, triazine, thiophene, furan, thiazole, thiadiazole, isothiazole, oxazole, oxadiazole, isooxazole, naphthalene, quinoline, tetralin, chroman, thiochroman, tetrahydroquinoline, dihydronaphthalene, tetrahydronaphthalen, chromene, thiochromene, dihydroquinoline, indan, dihydrobenzofuran, dihydrobenzothiophene, indene, benzofuran, benzothiophene, coumarin, coumarinone, and the like.

In certain embodiments, each Ar is independently phenyl, pyridine, thiophene, thiazole, or oxazole.

The compounds of the invention may contain a wide a variety of substituents. When invention compounds bear substituents, the substituents are typically selected from alkyl, alkenyl, alkynyl, hydroxy, alkoxy, heterocyclic, aryl, heteroaryl, aryloxy, halogen, haloalkyl, cyano, nitro, amino, lower alkylamino, lower dialkylamino, amido, azido, acyl (—C(O)R$_6$), alkoxymethyl, mercapto (—S—R$_6$), sulfoxy (—S(O)—R$_6$), sulfonyl (—S(O)$_2$—R$_6$), sulfonamide (—S(O)$_2$N(R$_6$)$_2$), carbonate (—OC(O)—O—R$_6$), oxyacyl (—OC(O)—R$_6$), carboxyl (—C(O)OH), ester (—C(O)OR$_6$), carbamate (—OC(O)—N(R$_6$)$_2$), wherein R$_6$ is H or lower alkyl, lower alkenyl, lower alkynyl, aryl, heteroaryl, heterocycle, and the like.

In some embodiments, the substituents are selected from alkyl, halogen, or haloalkyl. In certain embodiments, the substituents are fluoro or trifluoromethyl.

Exemplary compounds according to the invention include, but are not limited to, compounds having the structure:

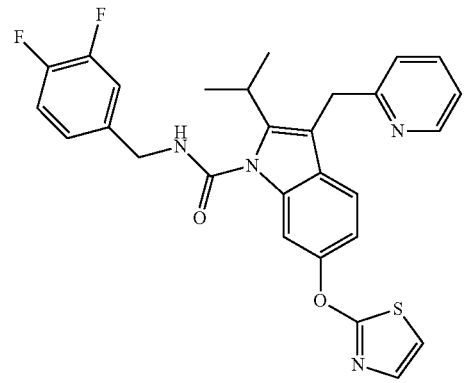

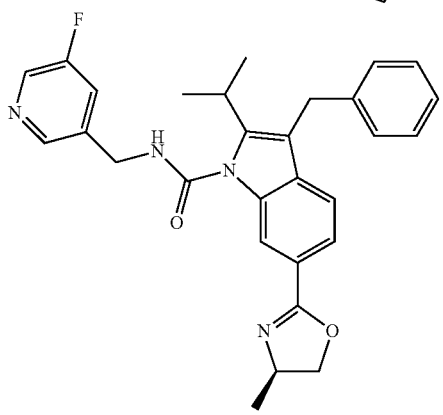

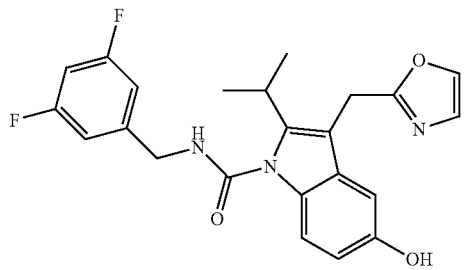

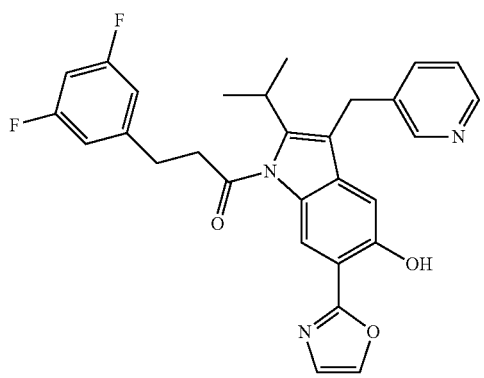

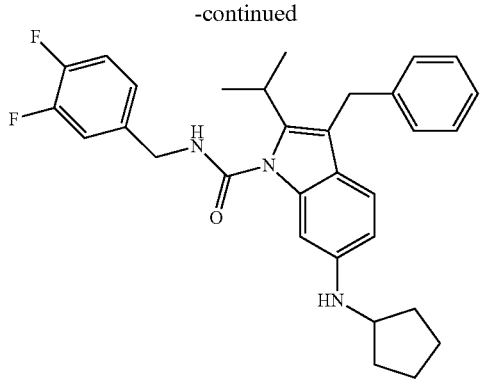
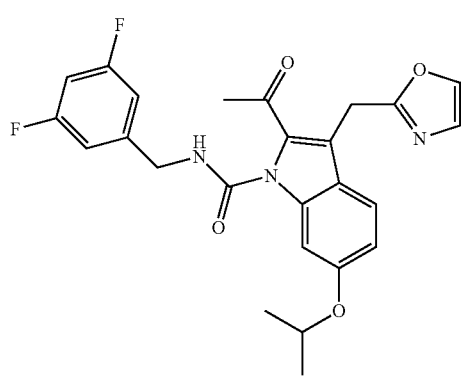
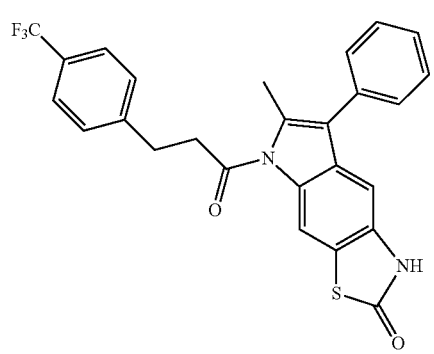
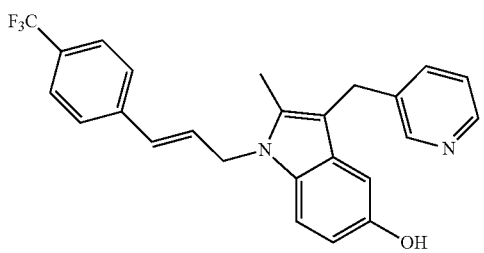
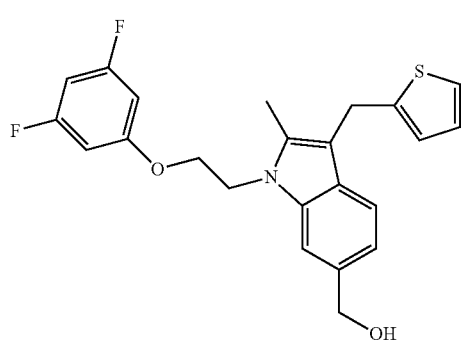
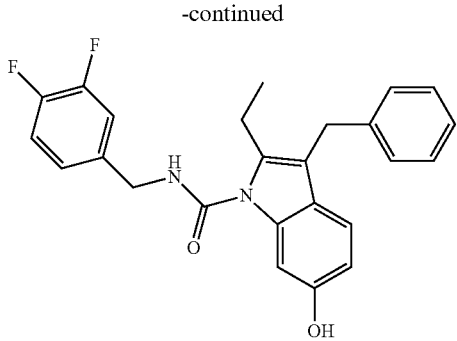
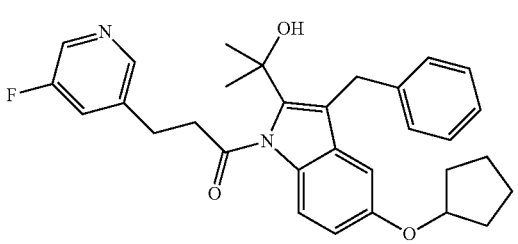
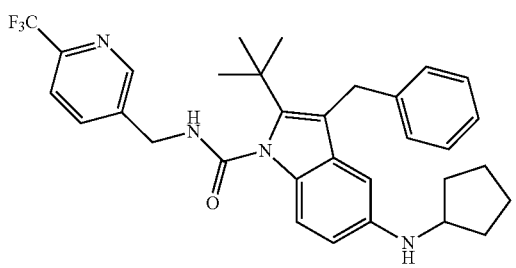
The compounds of the invention can be prepared in a variety of ways well known to those skilled in the art. Scheme A set forth below outlines an exemplary synthetic route to the compounds of the invention.
Scheme A
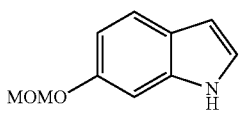
1) t-BuN=C=O
2) t-BuLi
3) RBr
4) LiOH, MeOH
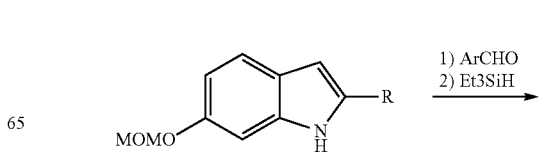
1) ArCHO
2) Et3SiH

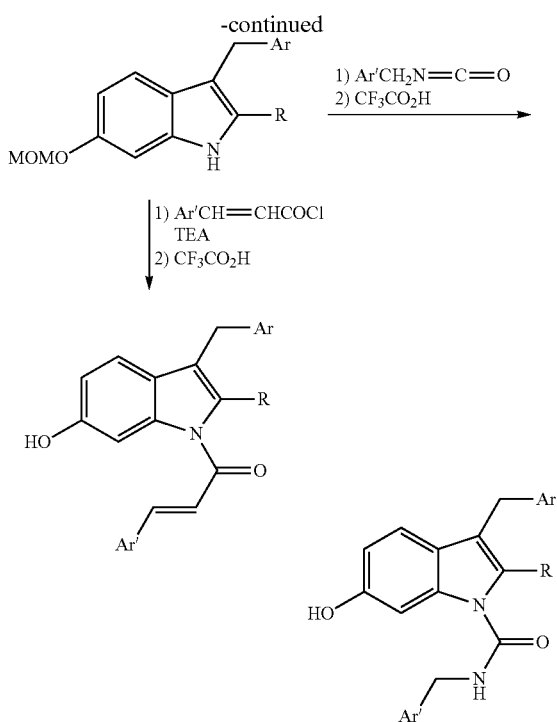

Diseases that may be treated with the compounds, compositions, and methods of the invention include, but are not limited to the following conditions:

Pain
S1P increases capsaicin responsiveness of DRG neurons
S1P pathway, S1P3, S1P1 deregulated in multiple pain models (EHT/AGN)

Glaucoma
S1P3 subtypes are expressed in primary human trabecular meshwork cells and S1P decreases outflow facility >30% in perfused porcine eyes (See IOVS 45, 2263; 2004) by altering paracellular permeability.

Dry Eye/Immunology
Induces lymphocyte sequestration without affecting T cell proliferation.

Angiogenesis Disorders
S1P3 receptor subtype is expressed in vascular endothelial cells and siRNA knockdown of S1P1 and S1P3 inhibits angiogenesis. S1P also promotes vascular endothelial cell migration and promotes barrier assembly and integrity.

Cardiovascular (S1P3)
S1P3 "knock out" mice lack S1P induced pulmonary edema.

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Both acute pain and chronic pain may be treated by administration of the compounds and compositions of the invention. By "acute pain" is meant immediate, usually high threshold, pain brought about by injury such as a cut, crush, burn, or by chemical stimulation such as that experienced upon exposure to capsaicin, the active ingredient in chili peppers. By "chronic pain" is meant pain other than acute pain, such as, without limitation, neuropathic pain, visceral pain (including that brought about by Crohn's disease and irritable bowel syndrome (IBS)), and referred pain.

Preferably, the patient will be administered the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more aryl and/or heteroaryl substituted indoles of the present invention, as an active ingredient, in admixture with an organic or inorganic carrier or excipient suitable for enteral or parenteral applications. Invention aryl and/or heteroaryl substituted indoles may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention aryl and/or heteroaryl substituted indoles are included in the pharmaceutical composition in an amount sufficient to produce the desired effect upon the process or disease condition.

Pharmaceutical compositions containing invention aryl and/or heteroaryl substituted indoles may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention aryl and/or heteroaryl substituted indoles in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention aryl and/or heteroaryl substituted indoles may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists or antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

What is claimed is:

1. A compound having the structure:

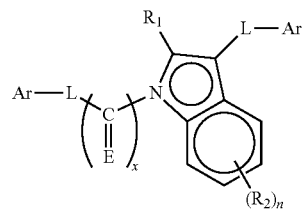

wherein:
each Ar is independently substituted or unsubstituted phenyl or pyridine or thiophene or oxazole;
each L is independently alkylene, alkenylene, oxyalkylene, oxyalkenylene, aminoalkylene, or aminoalkenylene;
$R_1$ is lower alkyl or alkylacyl or hydroxyalkyl;
each $R_2$ is independently H, lower alkyl, halide, trifluoromethyl, lower alkenyl, lower alkynyl, cycloalkyl, —CN, —CH$_2$CN, —CH$_2$SR$_3$, —CH$_2$N(R$_3$)$_2$, —CH$_2$OR$_3$, —CH=NOR$_3$, —OR$_3$, —SR$_3$, —N(R$_3$)$_2$, —C(O)R$_4$, heterocycle, substituted heterocycle, aryl, substituted aryl, heteroaryl, substituted heteroaryl; or
$R_2$ is

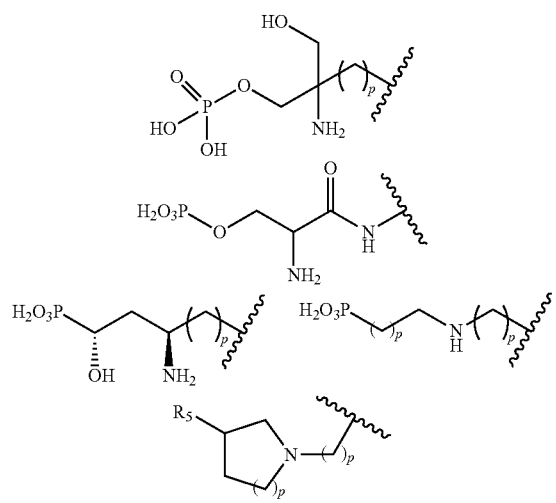

wherein $R_5$ is —CO$_2$H or PO$_3$H$_2$ and p is 0-2; or
when n is 2, each $R_2$ taken together with carbon atoms to which each $R_2$ is attached forms an aryl, substituted aryl, heteroaryl, substituted heteroaryl, cycloalkyl or substituted cycloalkyl;
each $R_3$ is independently H, lower alkyl, cycloalkyl, allyl, phenyl, substituted phenyl, heteroaryl, or substituted heteroaryl;
each $R_4$ is independently H, lower alkyl, cycloalkyl, alkoxy, alkylamino, dialkylamino, phenyl, substituted phenyl, heteroaryl, substituted heteroaryl, or trifluoromethyl;
E is O
x is 1; and
n is 0-5;
or a pharmaceutically acceptable salt thereof.

2. The compound of claim 1, wherein each Ar is independently selected from phenyl, pyridine.

3. The compound of claim 1, wherein each substituted phenyl or substituted heteroaryl-bears substituents selected from alkyl, alkenyl, alkynyl, hydroxy, oxo, alkoxy, mercapto, cycloalkyl, heterocyclic, aryl, heteroaryl, aryloxy, halogen, haloalkyl, cyano, nitro, amino, lower alkylamino, lower dialkylamino, amido, acyl (—C(O)$R_6$), alkoxymethyl, mercapto (—S—$R_6$), sulfoxy (—S(O)—$R_6$), sulfonyl (—S(O)$_2$—$R_6$), sulfonamide (—S(O)$_2$N($R_6$)$_2$), carbonate (—OC(O)—O—$R_6$), oxyacyl (—OC(O)—$R_6$), carboxyl (—C(O)OH), ester (—C(O)O$R_6$), carbamate (—OC(O)—N($R_6$)$_2$), wherein $R_6$ is H or lower alkyl, lower alkenyl, lower alkynyl, aryl, heteroaryl, or heterocycle.

4. The compound of claim 3, wherein the substituents are selected from alkyl, halogen, or haloalkyl.

5. The compound of claim 4, wherein the substituents are fluoro or trifluoromethyl.

6. The compound of claim 1, having any one of the structures:

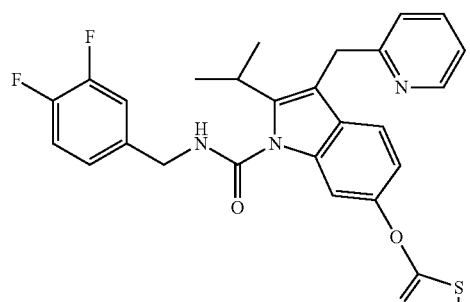

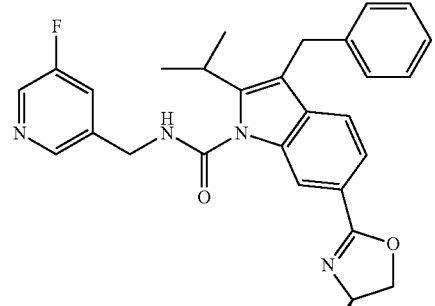

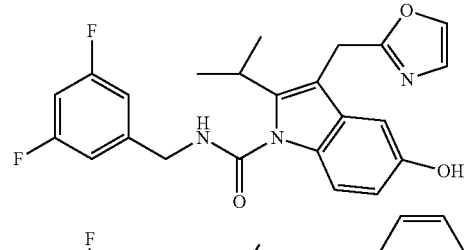

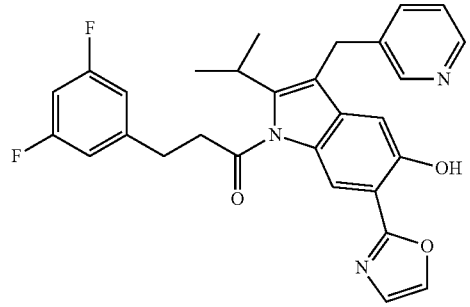

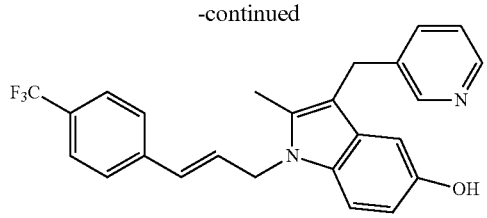

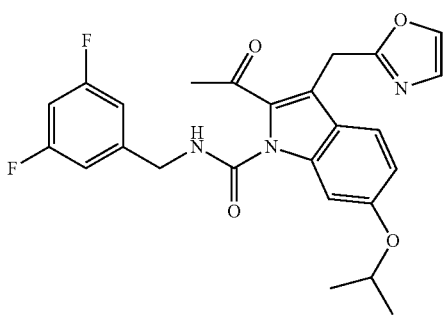

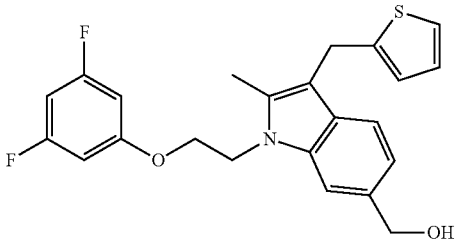

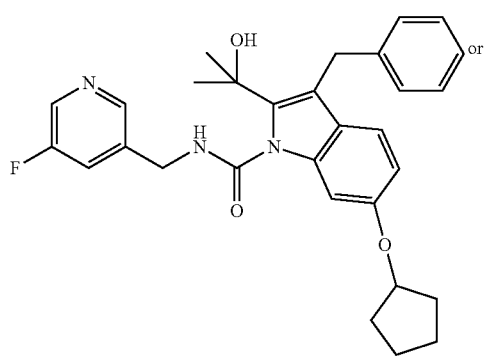

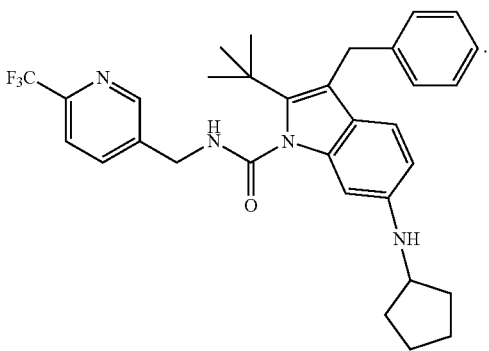

7. A pharmaceutical composition comprising at least one compound of claim 1 in a pharmaceutically acceptable carrier thereof.

* * * * *